US00PP26141P2

(12) United States Plant Patent
Noort

(10) Patent No.: US PP26,141 P2
(45) Date of Patent: Nov. 24, 2015

(54) ***GERANIUM* PLANT NAMED 'PINK POUFFE'**

(50) Latin Name: *Geranium sanguineum*
Varietal Denomination: Pink Pouffe

(71) Applicant: Marco van Noort Breeding BV, Warmond (NL)

(72) Inventor: Marco van Noort, Warmond (NL)

(73) Assignee: MARCO VAN NOORT BREEDING BV, Warmond (NL)

( * ) Notice: Subject to any disclaimer, the term of this patent is extended or adjusted under 35 U.S.C. 154(b) by 123 days.

(21) Appl. No.: 13/987,672

(22) Filed: Aug. 20, 2013

(51) Int. Cl.
*A01H 5/00* (2006.01)

(52) U.S. Cl.
USPC ..... Plt./324

(58) Field of Classification Search
USPC ..... Plt./324
See application file for complete search history.

*Primary Examiner* — Keith Robinson
(74) *Attorney, Agent, or Firm* — Penny J. Aguirre

(57) ABSTRACT

A new cultivar of *Geranium sanguineum*, 'Pink Pouffe', that is characterized by its compact plant habit, its floriferous blooming habit, its light pink flowers, and its early and long blooming period.

2 Drawing Sheets

Botanical classification: *Geranium sanguineum.*
Cultivar designation: 'Pink Pouffe'.

BACKGROUND OF THE INVENTION

The present invention relates to a new and distinct cultivar of *Geranium* plant, botanically known as *Geranium sanguineum* 'Pink Pouffe' and will be referred to hereafter by its cultivar name, 'Pink Pouffe'.

The new cultivar was derived from a controlled breeding program by the Inventor in Warmond, The Netherlands. The Inventor made a cross in summer of 2007 between an unnamed proprietary plant of *Geranium sanguineum* from the Inventor's breeding program as the female parent and *Geranium sanguineum* var. *striatum* (not patented) as the male parent. The Inventor selected 'Pink Pouffe' in July of 2009 as a single unique plant amongst the seedlings that resulted from the above cross.

Asexual propagation of the new cultivar was first accomplished by root cuttings in Warmond, The Netherlands in February 2010 by the Inventor. Asexual propagation by root cuttings and subsequently by tissue culture has determined that the characteristics of the new cultivar are stable and are reproduced true to type in successive generations.

SUMMARY OF THE INVENTION

The following traits have been repeatedly observed and represent the characteristics of 'Pink Pouffe'. These attributes in combination distinguish 'Pink Pouffe' as a new and distinct cultivar of *Geranium.*

1. 'Pink Pouffe' exhibits a compact plant habit.
2. 'Pink Pouffe' exhibits a floriferous blooming habit.
3. 'Pink Pouffe' starts flowering early in the season in April in The Netherlands.
4. 'Pink Pouffe' exhibits a long bloom period; blooming into September in The Netherlands.
5. 'Pink Pouffe' exhibits light pink flowers.

The female parent of 'Pink Pouffe', a proprietary seedling, differs from 'Pink Pouffe' in having a less compact plant habit, in being less floriferous, in commencing bloom later in the season and in having a shorter bloom period. The male parent of 'Pink Pouffe', a proprietary seedling, differs from 'Pink Pouffe' in having a less compact plant habit, a shorter bloom period, and slightly larger flowers and in being less floriferous. 'Pink Pouffe' can be most closely compared to the cultivars 'Cedric Morris' (not patented) and 'Max Frei' (not patented). 'Cedric Morris' differs from 'Pink Pouffe' in having a less compact plant shape, flowers that are deeper pink in color, and in commencing bloom later in the season. 'Max Frei' differs from 'Pink Pouffe' in having a less compact plant shape, flowers that are dark purple-red in color, and in commencing bloom later in the season.

BRIEF DESCRIPTION OF THE DRAWINGS

The accompanying colored photographs illustrate the overall appearance and distinct characteristics of the new *Geranium*. The photographs were taken of a one year-old plant of 'Pink Pouffe' as grown outdoors in a field plot in Warmond, The Netherlands.

The photograph in FIG. 1 provides a view of the compact plant habit of 'Pink Pouffe'.

Figure 1:
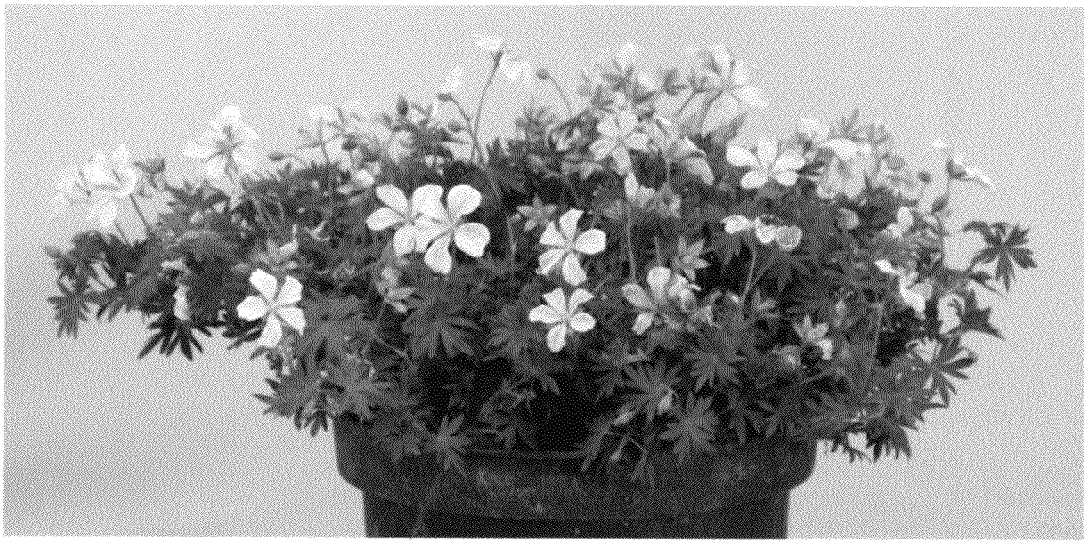
Figure 2:
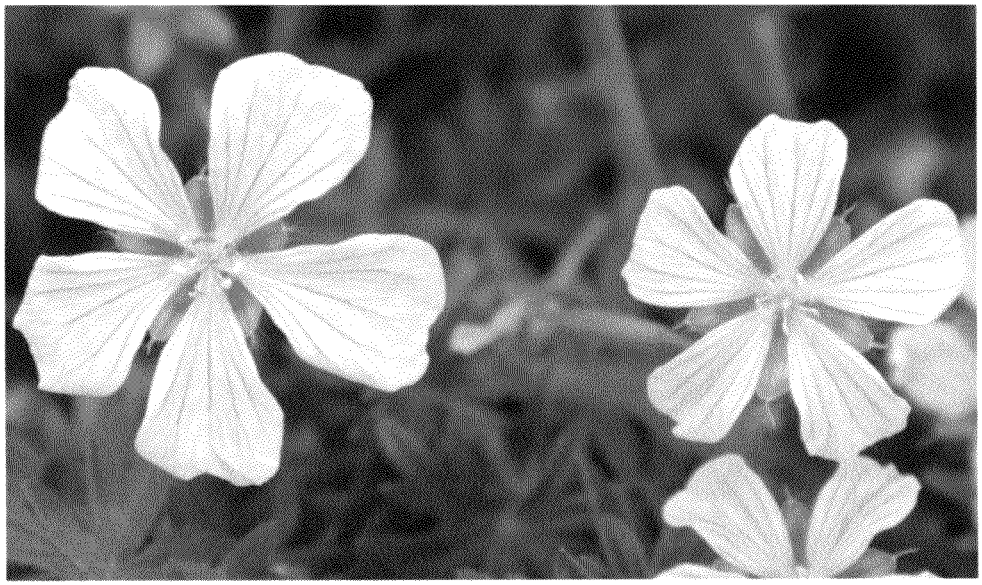

The photograph in FIG. 2 provides a close-up view of the flowers of 'Pink Pouffe'.

Figure 3:
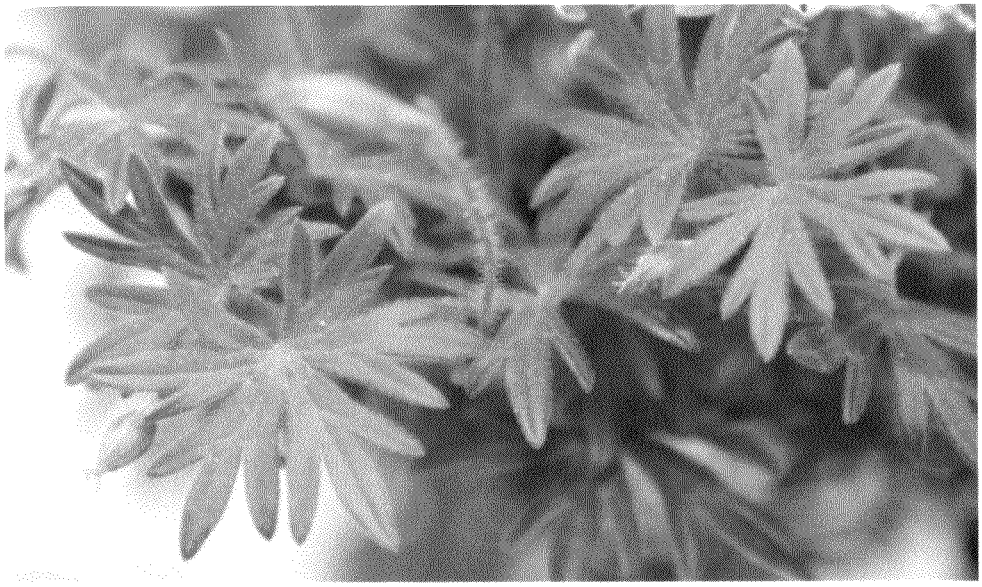

The photograph in FIG. 3 provides a close-up view of the foliage of 'Pink Pouffe'.

The colors in the photographs are as close as possible with the photographic and printing technology utilized and the color values cited in the detailed botanical description accurately describe the colors of the new *Geranium.*

DETAILED BOTANICAL DESCRIPTION OF THE PLANT

The following is a detailed description of one year-old plants of the new cultivar as grown outdoors in a field plot in Warmond, The Netherlands. Plants were grown under average day temperatures of 15° to 28° C. and average night temperatures of 6° to 15° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Early and long blooming; blooming from April into September in The Netherlands.

*Plant type.*—Herbaceous perennial.

*Plant habit.*—Compact.

*Height and spread.*—Reaches an average of 20 cm in height and 30 cm in spread.

*Cold hardiness.*—At least to U.S.D.A. Zone 5.

*Heat tolerance.*—At least tolerant to temperature up to 35° C.

*Diseases and pests.*—Not more susceptible or resistant to pests and diseases than other *Geranium* varieties.

*Root description.*—Fibrous roots extending from stout rootstock.

*Branching habit.*—Freely branched, about 46 lateral branches on a 1 year-old plant.

*Growth rate.*—Moderate.

*Propagation.*—Root cuttings and tissue culture.

Stem description:

*Stem size.*—Average of 12.3 cm in length and 1.5 mm in width.

*Stem shape.*—Round.

*Stem strength.*—Moderately strong.

*Stem color.*—Upper and lower surface; 144A to 144B.

*Stem surface.*—Slightly glossy, moderately pubescent; covered with soft hairs an average of 1 mm in length and NN155D in color.

*Internode length.*—Average of 2.4 cm.

Foliage description:

*Leaf shape.*—Reniform (in outline), palmately deeply cleft to parted with an average of five lobes.

*Leaf division.*—Simple.

*Leaf base.*—Hastate.

*Leaf apex.*—Acute.

*Leaf venation.*—Palmate, 144B in color on upper surface and 143A on lower surface.

*Leaf margins.*—Palmately deeply cleft to parted into an average of five lobes; margins of lobes incised.

*Leaf attachment.*—Petiolate.

*Leaf arrangement.*—Opposite.

*Leaf surface.*—Upper surface; slightly glossy and moderately covered with short and soft adpressed hairs; an average of 0.5 mm in length and NN155D in color, lower surface; slightly glossy and moderately covered with short soft hairs (especially on main secondary veins); an average of 1 mm in length, NN155D in color.

*Leaf color.*—Young upper surface; 137B, young lower surface; 143A, mature upper surface; N137B, mature lower surface; 137C.

*Leaf size.*—Average of 2.6 cm in length and 3.2 cm in width.

*Leaf quantity.*—Average of 12 (6 pairs) per lateral branch.

*Petiole size.*—Average of 1.7 cm in length and 0.8 mm in width.

*Petiole color.*—145A.

*Petiole strength.*—Strong.

*Stipules.*—A leafy stipule is present at the base of basal leaves, ovate in shape, acute apex, an average of 2 mm in length and 1.5 mm in width, 161A in color.

Flower description:

*Inflorescence type.*—Single, rotate.

*Lastingness of flowers.*—About 7 days, self cleaning.

*Flower size.*—Average of 9 mm in height and 3.2 cm in diameter.

*Flower fragrance.*—None.

*Flower number.*—Average of 1 per lateral stem, an average of 320 per plant.

*Flower aspect.*—Outward to upright.

*Flower bud size.*—Average of 8 mm in length, up to 4 mm in width.

*Flower bud color.*—144C, veined darker; 138A, densely covered with short soft hairs and average length of 1 mm and NN155D in color.

*Flower bud surface.*—Glabrous.

*Flower bud shape.*—Elliptic.

*Corolla features.*—Petals are un-fused and arranged in a rotate form.

*Petal number.*—5.

*Petal shape.*—Obcordate, slightly concave.

*Petal color.*—Opening, upper and lower surface; 84C with veins N57C, fully open, upper and lower surface; lighter than 84C with veins 64C, color not fading.

*Petal surface.*—Glabrous on upper and lower surface.

*Petal margins.*—Entire.

*Petal apex.*—Retuse.

*Petal size.*—Average of 1.7 cm in length and 1.2 cm in width.

*Calyx form.*—Rotate, cupped.

*Calyx size.*—Average of 7 mm in length and 1.6 cm in width.

*Sepal number.*—Average of 5.

*Sepal shape.*—Ovate.

*Sepal margin.*—Entire.

*Sepal size.*—Average of 1.1 mm cm length, 3.5 mm in width.

*Sepal surface.*—Dull on upper and lower surface.

*Sepal apex.*—Mucronate.

*Sepal base.*—Cuneate.

*Sepal color.*—Immature upper surface 144C and lower surface 144C with veins 138A, mature upper surface 144A and lower surface 144A with veins 138A.

*Peduncle size.*—Average of 5 cm in length and 1 mm in diameter.

*Peduncle strength/aspect.*—Strong, held at an angle of 30° (0°=straight on top of lateral branch).

*Peduncle color.*—144A.

*Pedicels.*—Not present.

Reproductive organs:

*Gynoecium.*—1 pistil, about 6 mm in length, 5 stigmas are decurrent and 153D in color, style is about 4 mm in length and 146C in color, ovary is 144A.

*Androcoecium.*—10 stamens, anthers are dorsifixed, oblong in shape, 1.5 mm in length, and 4C in color, filament is 6 mm in length and 186C in color with base NN155D, pollen is very low in quantity and 198D in color.

*Fruit/seeds.*—None detected.

It is claimed:

1. A new and distinct cultivar of *Geranium* plant named 'Pink Pouffe' as herein illustrated and described.

* * * * *